(12) United States Patent
Kawabata et al.

(10) Patent No.: US 11,612,368 B2
(45) Date of Patent: Mar. 28, 2023

(54) BIOMETRIC INFORMATION MEASURING DEVICE

(71) Applicants: National University Corporation Tokyo Medical and Dental University, Tokyo (JP); TDK CORPORATION, Tokyo (JP)

(72) Inventors: Shigenori Kawabata, Tokyo (JP); Tomohiko Shibuya, Tokyo (JP); Shuichi Okawa, Tokyo (JP)

(73) Assignees: National University Corporation Tokyo Medical and Dental University, Tokyo (JP); TDK CORPORATION, Tokyo (JP)

( * ) Notice: Subject to any disclaimer, the term of this patent is extended or adjusted under 35 U.S.C. 154(b) by 858 days.

(21) Appl. No.: 16/337,258

(22) PCT Filed: Sep. 29, 2017

(86) PCT No.: PCT/JP2017/035555
§ 371 (c)(1),
(2) Date: Mar. 27, 2019

(87) PCT Pub. No.: WO2018/062512
PCT Pub. Date: Apr. 5, 2018

(65) Prior Publication Data
US 2019/0223817 A1 Jul. 25, 2019

(30) Foreign Application Priority Data
Sep. 30, 2016 (JP) .............................. JP2016-192580

(51) Int. Cl.
*A61B 6/00* (2006.01)
*G01T 1/17* (2006.01)
(Continued)

(52) U.S. Cl.
CPC .............. *A61B 6/4417* (2013.01); *A61B 5/05* (2013.01); *A61B 5/242* (2021.01); *A61B 6/00* (2013.01);
(Continued)

(58) Field of Classification Search
None
See application file for complete search history.

(56) References Cited

U.S. PATENT DOCUMENTS

| | | | |
|---|---|---|---|
| 5,794,620 A | 8/1998 | Dossel et al. | |
| 6,522,908 B1 | 2/2003 | Miyashita et al. | |

(Continued)

FOREIGN PATENT DOCUMENTS

| | | |
|---|---|---|
| EP | 1987769 A1 | 11/2008 |
| EP | 3289978 A1 | 3/2018 |

(Continued)

OTHER PUBLICATIONS

"Adachi et al.," "A SQUID system for measurement of spinal cord evoked filed of supine subjects," IEEE Transactions on Applied Superconductivity, col. 19 No. 3, pp. 861-866, Jun. 2009.*

(Continued)

*Primary Examiner* — Patricia J Park
(74) *Attorney, Agent, or Firm* — Osha Bergman Watanabe & Burton LLP

(57) ABSTRACT

The present invention provides a biometric information measuring device with which a diagnostic imaging result and a biomagnetism measurement result can be superimposed simply and with satisfactory accuracy, and which is easy to handle. This biometric information measuring device (1) is provided with: a biomagnetism detecting unit (2) capable of detecting biomagnetism of a subject (S); and a radiation detecting unit (3) capable of acquiring an image corresponding to irradiated radiation, as digital image data, (Continued)

by means of the supply of a power source. The radiation detecting unit (3) is disposed between a measuring region of the subject (S) and the biomagnetism detecting unit (2). Further, it is preferable to provide a control unit (6) capable of performing control such that the power source is not supplied to the radiation detecting unit (3) while the biomagnetism detecting unit (2) is detecting biomagnetism.

14 Claims, 4 Drawing Sheets

(51) Int. Cl.
  *G01R 33/06* (2006.01)
  *A61B 6/04* (2006.01)
  *A61B 5/05* (2021.01)
  *A61B 5/242* (2021.01)
(52) U.S. Cl.
  CPC .............. *A61B 6/04* (2013.01); *A61B 6/0407* (2013.01); *A61B 6/42* (2013.01); *A61B 6/5247* (2013.01); *G01R 33/06* (2013.01); *G01T 1/17* (2013.01)

(56) References Cited

U.S. PATENT DOCUMENTS

| | | | |
|---|---|---|---|
| 6,628,978 | B1 | 9/2003 | Kondo et al. |
| 8,583,208 | B2 | 11/2013 | Adachi et al. |
| 2009/0012384 | A1 | 1/2009 | Adachi et al. |
| 2009/0018431 | A1 | 1/2009 | Feiweier et al. |
| 2011/0152676 | A1* | 6/2011 | Groszmann .......... A61B 6/5235 600/426 |

FOREIGN PATENT DOCUMENTS

| | | |
|---|---|---|
| JP | H02249530 A | 10/1990 |
| JP | H05184552 A | 7/1993 |
| JP | H07313561 A | 12/1995 |
| JP | 2001037761 A | 2/2001 |
| JP | 2006296520 A | 11/2006 |
| JP | 2007147604 A | 6/2007 |
| JP | 2009172175 A | 8/2009 |
| WO | 9949781 A1 | 10/1999 |
| WO | 2006122278 A2 | 11/2006 |
| WO | 2007099697 A1 | 9/2007 |
| WO | 2008127720 A2 | 10/2008 |
| WO | 2016175020 A1 | 11/2016 |

OTHER PUBLICATIONS

International Search Report issued for PCT/JP2017/035555, dated Oct. 31, 2017 (6 pages).
Written Opinion issued for PCT/JP2017/035555, dated Oct. 31, 2017 (4ages).
Extended European Search Report issued in the EP Patent Application No. EP17856459.7, dated May 25, 2020 (7 pages).
Supplementary European search report issued in European Patent Application No. 16786297.8, dated May 4, 2018 (4 pages).
Office Action issued to European Patent Application No. 16786297.8, dated May 25, 2018 (6 pages).
International Search Report issued in the International Application No. PCT/JP2016/061734 dated Jul. 12, 2016 (3 pages).
Written Opinion issued in the International Application No. PCT/JP2016/061734 dated Jul. 12, 2016 (6 pages).

* cited by examiner

BIOMETRIC INFORMATION MEASURING DEVICE

TECHNICAL FIELD

The present invention relates to a biometric information measuring device.

BACKGROUND ART

A biomagnetism measuring device is a device that measures weak biomagnetism emitted from the heart, spine or peripheral nerves of a subject and is able to detect magnetism generated by microcurrents as a result of excitation of the cells that make up the above-described organs. This type of device is an important type of technology used for diagnosing heart diseases and nervous disease.

In some cases, a diagnostic imagining device (for example, an X-ray irradiation apparatus that uses a film such as that described in Patent Document 1) in a different location to the biomagnetism measuring device takes a form image that is superimposed on results obtained by the biomagnetism measuring device.

Patent Document 1: Japanese Unexamined Patent Application, Publication No. 2009-172175

DISCLOSURE OF THE INVENTION

Problems to be Solved by the Invention

However, there is a problem in terms of accurately matching up the measurement results because the subject moves between the diagnostic imaging device (the X-ray irradiation apparatus or another apparatus) and the biomagnetism measuring device. When the subject moves between the X-ray irradiation apparatus and the biomagnetism measuring device, for example, the trunk (spine) of the subject bends and deforms in front/back and left/right directions, or the joints in the limbs of the subject bend and extend. Because of this, it is extremely difficult to accurately match positional information on the subject obtained by the diagnostic imaging device and positional information on the subject during examination with the biomagnetism measuring device.

The present invention has been made in light of the aforementioned problem, and it is an object of the present invention to provide an easy-to-use biometric information measuring device with which diagnostic imaging results and biomagnetic measurement results can be accurately and easily superimposed.

Means for Solving the Problems

The inventors of the present invention found that a so-called digital panel device for detecting X-rays configured to acquire emitted radiation as digital image data can detect X-rays even when placed between a magnetic sensor for detecting biomagnetism and a subject. Thus, the present invention was completed. More specifically, the present invention provides the following.

(1) A biometric information measuring device including: a biomagnetism detection unit that can detect biomagnetism of a subject; and a radiation detection unit that can acquire an image corresponding to emitted radiation as digital image data generated by means of the supply of a power source, the radiation detection unit being disposed between a measuring region of the subject and the biomagnetism detection unit.

(2) The biometric information measuring device according to (1), further including a control unit that can perform control such that the radiation detection unit is not supplied with power while the biomagnetism detection unit is detecting biomagnetism.

(3) The biometric information measuring device according to (1) or (2), in which the radiation detection unit is held by the biomagnetism detection unit.

(4) The biometric information measuring device according to any one of (1) to (3), further including a support stand that slidably supports the biomagnetism detection unit.

(5) The biometric information measuring device according to any one of (1) to (4), further including a support portion that supports the biomagnetism detection unit, the support portion including a support surface that can support the subject at an inclined posture.

(6) The biometric information measuring device according to (5), in which the support portion includes an angle adjustment mechanism that can adjust an angle of the support surface from a horizontal direction.

(7) The biometric information measuring device according to any one of (1) to (6), further including a radiation emission unit that irradiates the subject with radiation.

(8) The biometric information measuring device according to any one of (1) to (7), in which the biomagnetism detection unit includes a plurality of magnetic sensors that can detect biomagnetism of the subject under a normal temperature environment.

(9) The biometric information measuring device according to any one of (1) to (8), in which the biomagnetism detection unit includes removable magnetic sensors.

Effects of the Invention

According to the present invention, there can be provided an easy-to-use biometric information measuring device with which diagnostic imaging results and biomagnetic measurement results can be accurately and easily superimposed.

PREFERRED MODE FOR CARRYING OUT THE INVENTION

Embodiments of the present invention are described in detail below, but the present invention is not limited these embodiments and may be changed as appropriate without departing from the scope of the present invention.

<Biometric Information Measuring Device According to First Embodiment>

Figure 1:
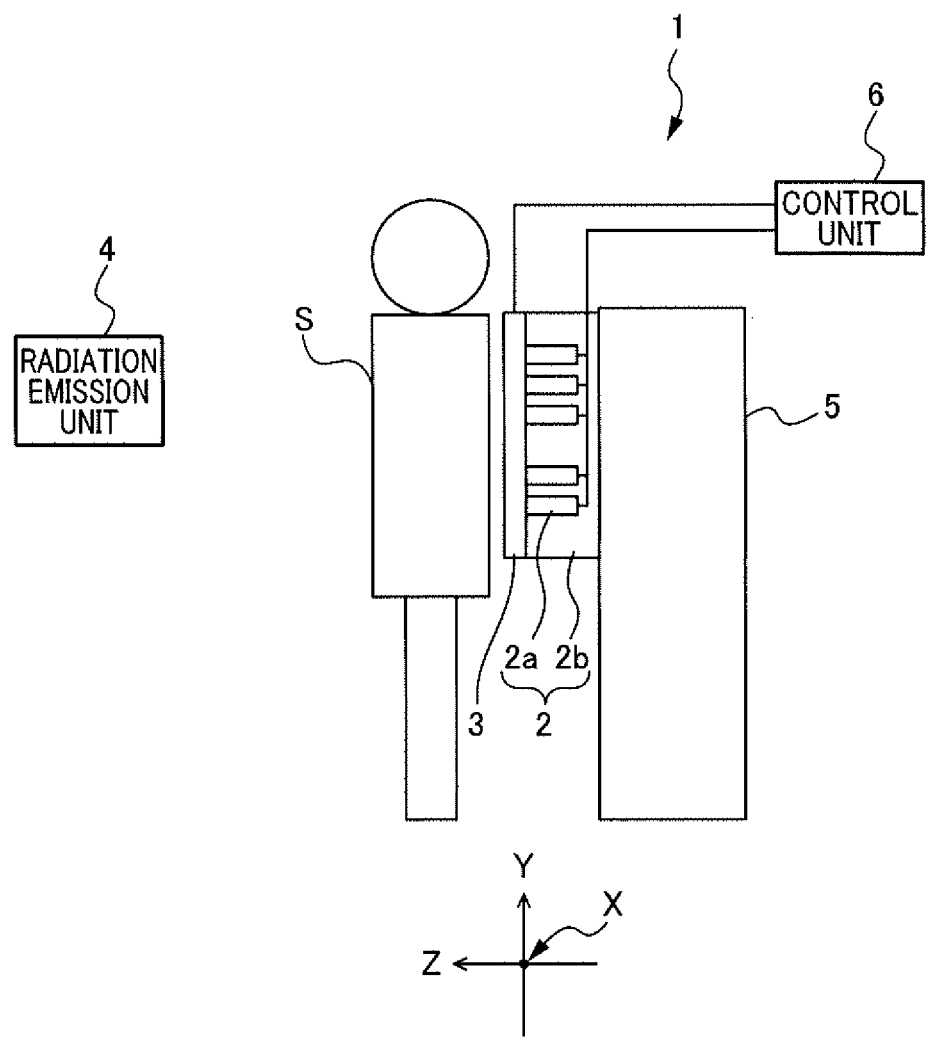
FIG. 1 is a configuration diagram for illustrating the configuration of a biometric information measuring device according to a first embodiment.

FIG. 1 is a configuration diagram for illustrating the configuration of a biometric information measuring device 1 according to a first embodiment. As illustrated in FIG. 1, the biometric information measuring device 1 includes a biomagnetism detection unit 2 that can detect biomagnetism of a subject S to be measured, and a radiation detection unit 3 that can acquire an image corresponding to emitted radiation as digital image data by means of the supply of a power source. The radiation detection unit 3 is disposed between a measuring region of the subject S and the biomagnetism detection unit 2. The biometric information measuring device 1 according to the present invention also includes a radiation emission unit 4 that irradiates the subject S with radiation.

With the biometric information measuring device 1 according to the first embodiment, biomagnetism detection results obtained from the biomagnetism detection unit 2 and the form image as digital image data obtained from the radiation detection unit 3 can be obtained in one measurement and accurately superimposed on each other.

The biomagnetism detection unit 2, the radiation detection unit 3, and the radiation emission unit 4 are now separately described.

[Biomagnetism Detection Unit]

The biomagnetism detection unit 2 includes a plurality of magnetic sensors 2a that can detect biomagnetism emitted from the subject S under a normal temperature environment, and a holding portion 2b that holds the magnetic sensors 2a. The holding portion 2b is made to a size that corresponds to the predetermined measuring region of the subject S. The plurality of magnetic sensors 2a are arranged in an array (for example, a 5×8 array) on a flat surface of the holding portion 2b that opposes the subject S. By providing the plurality of magnetic sensors 2a, a large amount of biomagnetic information can be obtained and more detailed biometric information can be acquired. The direction in which the magnetic sensors 2a are arrayed in the biomagnetism detection unit 2 and the number of magnetic sensors 2a are not particularly limited and may be set as required according to the measuring region of the subject S or the resolution.

The holding unit 2b is preferably made of a non-magnetic material. When the holding portion 2b is made of a non-magnetic material, the holding portion 2b is less likely to adversely affect results of detection by the biomagnetism detection unit 2. Further, even if the holding portion 2b vibrates, the influence of fluctuations in environmental magnetism on the magnetic sensors 2a can be minimized. Examples of a non-magnetic material include a plastic material such as an acrylic resin, and nonferrous metals such as copper and brass.

In order to dispose the biomagnetism detection unit 2 at the position that corresponds to the measuring region of the subject S, the biomagnetism detection unit 2 may be fixed to a support stand 5 or may be attached to the support stand 5 so as to allow the biomagnetism detection unit 2 to slide vertically and/or horizontally along the support stand 5. When the biomagnetism detection unit 2 is configured to slide relative to the support stand 5, the biomagnetism detection unit 2 can move to the position corresponding to the measuring region of the subject S and ease-of-use is improved. In addition, when the biomagnetism detection unit 2 is configured to slide relative to the support stand 5, the biomagnetism detection unit 2 can be made smaller and costs can be reduced. The biomagnetism detection unit 2 may be moved manually or automatically.

In the biometric information measuring device 1 according to the first embodiment, the support stand 5 may perform a function of placing a measurement subject as the subject S in an upright position at a predetermined position. For example, the support stand 5 may include gripping portions that the measurement subject is to grip with both upper limbs. The subject can stabilize themselves at the predetermined position by holding onto the gripping portions of the support stand 5 with both upper limbs (both hands).

(Magnetic Sensor)

The magnetic sensors 2a detect biomagnetism emitted from the subject S under a normal temperature environment. A "normal temperature environment" herein is an environment in which a temperature regulating mechanism for regulating the temperature of the magnetic sensors 2a is not required and may be, for example, indoors from −10° C. to 40° C. More specifically, the magnetic sensors 2a may be giant magnetoresistive sensors (GMR sensor), tunnel magnetoresistive sensors (TMR sensor), anisotropic magnetoresistive sensors (AMR sensor), magneto impedance sensors (MI sensor), or fluxgate sensors. The magnetic sensors 2a used in this embodiment may be any type of magnetic sensor provided that the magnetic sensors 2a can detect a magnetic field of from $10^{-4}$ T (tesla) to $10^{-10}$ T (tesla).

The detection means are not limited to the magnetic sensors 2a that can detect biomagnetism under a normal temperature environment and, for example, superconducting quantum interference devices (hereinafter referred to as "SQUID") may also be used. Although SQUID sensors need to be cooled with a refrigerant such as liquid helium or liquid nitrogen, SQUID sensors can detect magnetism with high precision.

However, as in the first embodiment, the plurality of magnetic sensors 2a used under a normal temperature environment can obtain the same amount of information as when using SQUID sensors if the plurality of magnetic sensors 2a are arranged in an array. Further, there is no need to provide a temperature regulating mechanism such as a cooling container as when using SQUID sensors, which means that the sensors are easier to handle and can be brought closer to the body.

The sensing direction of the magnetic sensors 2a is preferably parallel to at least one of an X-direction, a Y-direction and a Z-direction when a surface of the holding portion 2b that opposes the subject S forms an XY-plane in an XYZ orthogonal coordinate space and the normal direction of the opposing surface is the Z-direction. By making the sensing direction of the magnetic sensors 2a parallel to at least one of the X-direction, the Y-direction and the Z-direction, a magnetic field source and/or a current source can be accurately estimated from measurement data. Further, the biomagnetism detection unit 2 can acquired biomagnetic information obtained from at least two sensing directions in the XYZ orthogonal coordinate space, to thereby generate more accurate biomagnetic information. The sensing directions of the plurality of magnetic sensors 2a are preferably the same but may differ from each other. One magnetic sensor 2a may have a plurality of sensing directions.

Detection signals detected by the magnetic sensors 2a are sent to a calculation unit (not shown). The calculation unit generates biomagnetic information from the signals detected by the magnetic sensors 2a and visualizes the information to output and display the information on a display device.

The magnetic sensors 2a may be fixed to the holding portion 2b, or the magnetic sensors 2a may be removable from the holding portion 2b. The arrangement and number of the magnetic sensors 2a may be adjusted according to the shape and size of the measuring region of the subject S (for example, whether the subject is an adult, a child, or an animal other than a human). The required spatial resolution may vary depending on the measuring region of the subject S. Even in such a case, the magnetic sensors 2a may be removably attached to the holding portion 2b, to thereby dispose the magnetic sensors 2a close to a position (for example, the heart) that requires high space resolution and dispose the magnetic sensors 2a far from a position that does not require high space resolution. Through removably attaching the magnetic sensors 2a to the holding portion 2b, only necessary magnetic sensors 2a need to be provided, which means that signals are not transmitted/received and power is not supplied to unnecessary magnetic sensors 2a. As a result, power can be saved and costs can be lowered.

The magnetic sensors 2a may or may not have wiring that allows signals to be transmitted/received and power to be supplied. However, because a plurality of the magnetic sensors 2a are disposed in the biometric information measuring device 1 as illustrated in FIG. 2, it is preferable for the magnetic sensors 2a to have wiring in order to avoid interference.

Figure 2:
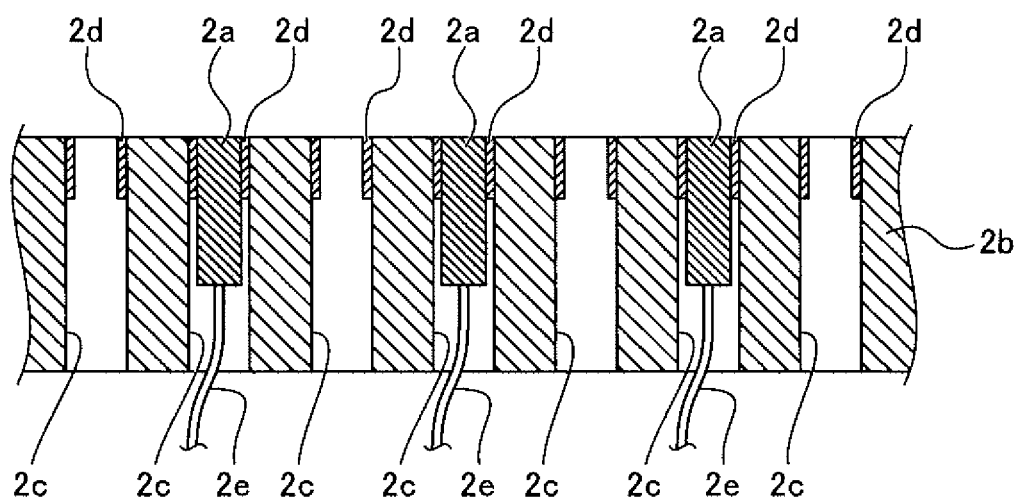
FIG. 2 is a schematic cross-sectional diagram for illustrating the configuration of a biomagnetism detection unit.

FIG. 2 is a schematic cross-sectional diagram for illustrating the configuration of the biomagnetism detection unit 2. For example, as illustrated in FIG. 2, a plurality of insertion holes 2c that can receive insertion of the magnetic sensors 2a and a plurality of frames 2d (fixing implements may be used as necessary) that can fix the detection surfaces of the magnetic sensors 2a at predetermined positions are formed in the holding portion 2b of the biomagnetism detection unit 2. As a result, the magnetic sensors 2a can be attached to/removed from the holding portion 2b at any desired position. The magnetic sensors 2a may further include wiring 2e.

[Radiation Detection Unit]

The radiation detection unit 3 is disposed between the measuring region of the subject S and the biomagnetism detection unit 2 and acquires an image corresponding to emitted radiation as a form image that is digital image data by means of the supply of a power source. Therefore, the form image can be obtained quickly and easily compared to when using a conventional radiation film. Detection results of biomagnetism and the form image can be easily superimposed to achieve images that are easier to use and store.

The signals detected by the radiation detection unit 3 is sent to a calculation unit (not shown). The calculation unit generates the form image from the signals detected by the radiation detection unit 3, visualizes the form image and outputs and displays the form image on a display device.

Incidentally, the magnetized radiation detection unit 3 greatly affects the results of detection by the biomagnetism detection unit 2 when disposed between the biomagnetism detection unit 2 and the subject S because the subject S only generates weak biomagnetism. As a result, the radiation detection unit 3 is made up of components that do not greatly affect the detection precision of the biomagnetism detection unit 2.

For example, a flat-panel detector (hereinafter referred to as "FPD") may be used as the radiation detection unit 3.

The FPD may use a so-called direct conversion method of generating charge with a detecting element according to the dose of irradiated radiation to convert the radiation to an electrical signal, or a so-called indirect method of using a scintillator to convert irradiated radiation to an electromagnetic wave with another wave length, such as visible light, and then generating charge using a photoelectric transducer such as a photodiode according to energy of the irradiated and converted electromagnetic wave to convert the radiation to an electrical signal. Generally speaking, various components that perform the above-described steps are built into the housing of the FPD (for example, a cassette). However, as described above, the radiation detection unit 3 is preferably not magnetized. Therefore, in the FPD used in the radiation detection unit 3 according to the present invention, various components that can be disposed outside the FPD, such as a circuit substrate that includes a plurality of magnetized bodies, a control substrate, and a battery, are preferably removed from the radiation detection unit 3 and disposed outside the FPD. Components made of metal such as the cassette are preferably made of a nonmagnetic material or are not used. As a result, the radiation detection unit 3 can be prevented from greatly affecting the detection accuracy of the biomagnetism detection unit 2 by way of resolution of components in the FPD or changing of the materials used to make the components. The subject S and the biomagnetism detection unit 2 are preferably disposed as close to each other as possible, and hence components that can be disposed outside are preferably removed from the radiation detection unit 3 and the thickness (direction orthogonal to the subject S) of the radiation detection unit 3 is preferably made as thin as possible. For example, the thickness of the FPD in the measuring region of the subject S is preferably no thicker than 10 mm, more preferably no thicker than 6 mm.

In terms of reducing the influence of the radiation detection unit 3 on the detection accuracy of the biomagnetism detection unit 2, the biometric information measuring device 1 preferably includes a control unit 6. The control unit 6 can perform control such that the radiation detection unit 3 is not supplied with power while the biomagnetism detection unit 2 detects biomagnetism. This control is performed because charge is generated in the radiation detection unit 3 which generates magnetism when power is supplied to the radiation detection unit 3, and this magnetism is detected by the biomagnetism detection unit 2. Therefore, through the control unit 6 controlling power supply to the radiation detection unit 3, the influence of the radiation detection unit 3 can be minimized. Power may or may not be supplied when acquiring detection results with the radiation detection unit 3 but, in terms of saving power, power is preferably not supplied.

The radiation detection unit 3 is preferably held by the biomagnetism detection unit 2 and fixed at a position relative to the biomagnetism detection unit 2. More specifically, the radiation detection unit 3 is preferably held on a surface of the holding portion 2b that opposes the subject S and fixed at a position relative to the biomagnetism detection unit 2. By fixing the radiation detection unit 3 at a position relative to the biomagnetism detection unit 2, biomagnetism detection results obtained from the biomagnetism detection unit 2 and the form image obtained from the radiation detection unit 3 can be accurately superimposed without having to provide position identification means for identifying positional information on both components.

The radiation detection unit 3 may be fixed to the biomagnetism detection unit 2 or may be removably held by the biomagnetism detection unit 2. For example, the holding portion 2b of the biomagnetism detection unit 2 may be provided with a rail mechanism, and the radiation detection unit 3 may be configured to removably engage with the rail. By making the radiation detection unit 3 removable, device maintenance is easier to perform. The radiation detection unit 3 may be removed if only results of detection by the biomagnetism detection unit 2 are required.

[Radiation Emission Unit]

Herein, the term "radiation" refers to a comprehensive concept that includes not only generally used X-rays but also alpha rays, beta rays, gamma rays and other rays as beams that consist of particles (including photons) that are emitted due to radioactive decay, and beams that have the same or higher energy such as particle beams and cosmic rays. In order to make the present invention more applicable, X-rays are preferably used as the radiation.

The radiation emission unit 4 may be any conventional and well-known radiation emitter provided that the radiation emission unit 4 can emit radiation that can irradiate a body. Herein, the radiation emission unit 4 can preferably move together with the sliding movement of the biomagnetism detection unit 2 when the radiation detection unit 3 is held by the biomagnetism detection unit 2 and the biomagnetism detection unit 2 slides relative to the support stand 5.

[Measurement Procedure]

As illustrated in FIG. 1, during an examination in which, for example, an X-ray of the chest of a subject (human) S is taken and biomagnetism is simultaneously measured, the subject (human) S stands at a predetermined measurement position by holding onto the gripping portions of the support stand 5 with both upper limbs. The person performing the examination irradiates the subject S with radiation from the radiation emission unit 4 and acquires an X-ray image as detection results from the radiation detection unit 3. Then, while the control unit 6 does not supply power to the radiation detection unit 3, power is supplied to the biomagnetism detection unit 2 to obtain a magnetocardiogram as detection results from the biomagnetism detection unit 2.

Alternatively, the person performing the examination may irradiate the subject S with radiation from the radiation emission unit 4 and obtain the X-ray image as detection results from the radiation detection unit 3 after power is supplied to the biomagnetism detection unit 2 while the control unit 6 does not supply power to the radiation detection unit 3 and the magnetocardiogram has been obtained as detection results from the biomagnetism detection unit 2.

X-ray images and magnetocardiograms may be continuously acquired and turned into a moving image. In the measurement illustrated in FIG. 1, the subject S is illustrated as standing facing the front of the support stand 5, but the subject S may stand with the back to the support stand 5 depending on the measuring region.

<Biometric Information Measuring Device According to Second Embodiment>

Figure 3:
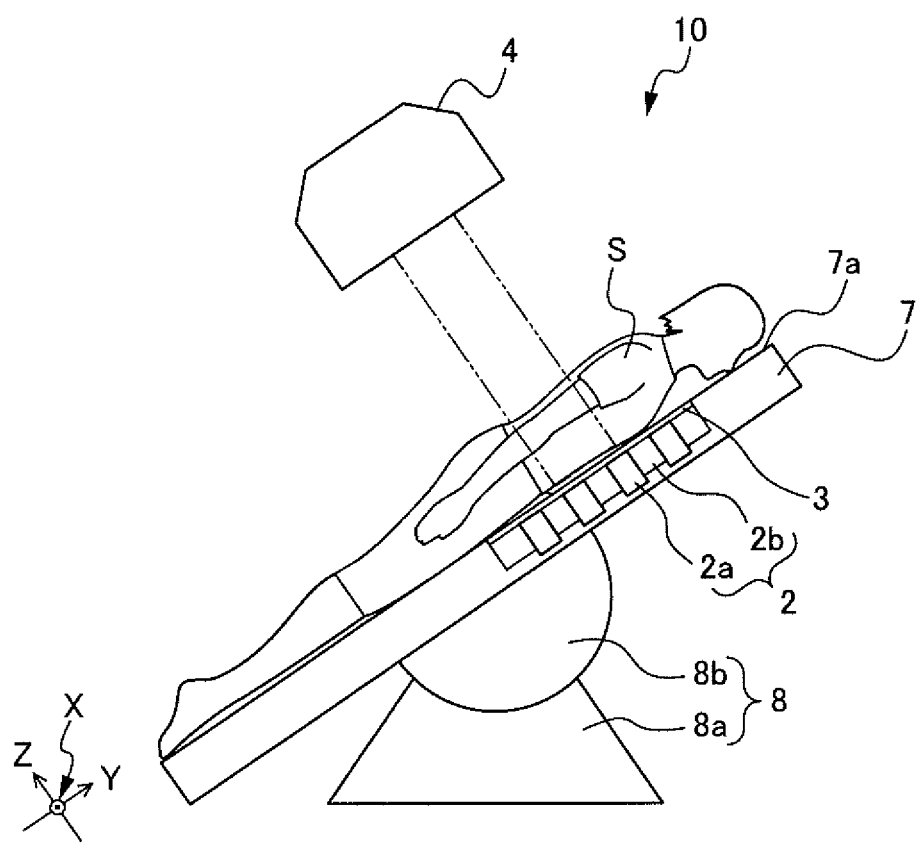
FIG. 3 is a configuration diagram for illustrating the configuration of a biometric information measuring device according to a second embodiment.

FIG. 3 is a configuration diagram for illustrating the configuration of a biometric information measuring device 10 according to a second embodiment. When describing the embodiment below, a description is only given for aspects different to the first embodiment. Components that are the same as those in the first embodiment are denoted by the same reference symbols and descriptions thereof are omitted. As illustrated in FIG. 3, the biometric information measuring device 10 according to the second embodiment includes the biomagnetism detection unit 2 with magnetic sensors 2a that can detect biomagnetism of the subject S, and the radiation detection unit 3 that can acquire an image corresponding to irradiated radiation as digital image data generated by means of the supply of a power source. The radiation detection unit 3 is disposed between the measuring region of the subject S and the biomagnetism detection unit 2. The biometric information measuring device 10 also includes the radiation emission unit 4 that irradiates the subject S with radiation, and a support portion 7 with a support surface 7a that supports the biomagnetism detection unit 2 and can support the subject S at an inclined posture.

With the biometric information measuring device 10 according to the second embodiment, the subject S can be supported at an inclined posture. As a result, biomagnetism detection results obtained from the biomagnetism detection unit 2 and the digital image data obtained from the radiation detection unit 3 can be safely acquired at the same time. The biometric information measuring device 10 is also compatible with cases where stable measurement is not possible during measurement that requires the subject to stand because the subject S is unsteady and finds it difficult to stand. In addition, it is possible to diagnose pleural effusion, which is part of a routine chest X-ray with the problems that are difficult to be diagnosed when the subject S assumes a lying position (lays down horizontally). Note that an "inclined posture" refers to neither a standing posture nor a lying posture (lying on back or front).

[Support Portion]

The support portion 7 includes the support surface 7a that can support the subject S in at inclined posture. More specifically, the support surface 7a of the support portion 7 is preferably horizontally inclined from 30° to 60°. The support portion 7 includes a mode of supporting the entire body of the subject S and a mode of supporting part (the measuring region) of the subject S.

Because the subject S is in an inclined posture on the support portion 7 during measurement, gravity acts on the subject S so that the subject S is stabilized and in close contact with the detection surface of the biomagnetism detection unit 2 disposed on part of the support surface 7a. Therefore, the biomagnetism detection unit 2 can detect stronger biomagnetism from the subject S. In addition, because the subject S is in an inclined posture, a pleural effusion in the lung of the subject S can be more easily detected by the radiation detection unit 3 and diagnosed. When the support surface 7a of the support portion 7 is horizontal, the subject S is stabilized and can be in close contact with the biomagnetism detection unit 2, but pleural effusions are more difficultly diagnosed.

The support surface 7a of the support portion 7 may be fixed at any angle in advance, or the support portion 7 may be provided with an angle adjustment mechanism 8 that can adjust the angle of the support surface 7a to any angle.

The support portion 7 illustrated in FIG. 3 includes the angle adjustment mechanism 8 that is made up of a pedestal 8a and a semi-circular rotational axis support frame 8b that is rotationally supported by the pedestal 8a. With the angle adjustment mechanism 8, the inclination of the support surface 7a can be adjusted to any angle. In addition, the rotational axis support frame 8b can be rotated in an anticlockwise direction in FIG. 3 by drive means (not shown), to thereby rotate the support portion 7 in the anticlockwise direction in FIG. 3 about the rotational axis support frame 8b and increase the inclination of the support surface 7a from the horizontal direction. On the other hand, when the rotational axis support frame 8b is rotated in a clockwise direction in FIG. 3 by the drive means (not shown), the support portion 7 rotates in the clockwise direction in FIG. 3 about the rotational axis support frame 8b to decrease the inclination of the support surface 7a from the horizontal direction. The radiation emission unit 4 can constantly emit radiation from a specific direction toward the subject S on the support portion 7 even if the support surface 7a is inclined.

The support portion 7 is not limited to a bed and may be the back of a seat. When the biomagnetism detection unit 2 and the radiation detection unit 3 are provided in the back of a seat, the back of the seat may be fixed inclined at any angle or may include a mechanism that can adjust the angle of the back of the seat to any angle.

[Measurement Procedure]

For example, for examination in which an X-ray of the chest of the subject (human) S is taken and biomagnetism is measured simultaneously as illustrated in FIG. 3, the subject S lays face up or face down on the support portion 7 that has a horizontal support surface 7a and waits at a predetermined position. The person performing the examination operates the angle adjustment mechanism 8 using an operation unit (not shown) to incline the support portion 7 (support surface 7a) to a particular angle. Then, the person performing the examination irradiates the subject S with radiation from the radiation emission unit 4 and obtains an X-ray image as detection results from the radiation detection unit 3. Then, the biomagnetism detection unit 2 is supplied with power while the radiation detection unit 3 is not supplied with power to obtain a magnetocardiogram as detection results from the biomagnetism detection unit 2.

Alternatively, the person performing the examination may irradiate the subject S with radiation from the radiation emission unit 4 and obtain the X-ray image as detection results from the radiation detection unit 3 after power is supplied to the biomagnetism detection unit 2 while power is not supplied to the radiation detection unit 3 to obtain the magnetocardiogram as detection results from the biomagnetism detection unit 2. After the biomagnetism has been detected or the X-ray image has been taken, the person performing the examination operates the angle adjustment mechanism 8 and returns the support portion 7 to a horizontal position. An examination is finished when the support portion 7 has been returned to a position at which the subject S can easily come down from the support portion 7.

Figure 4:
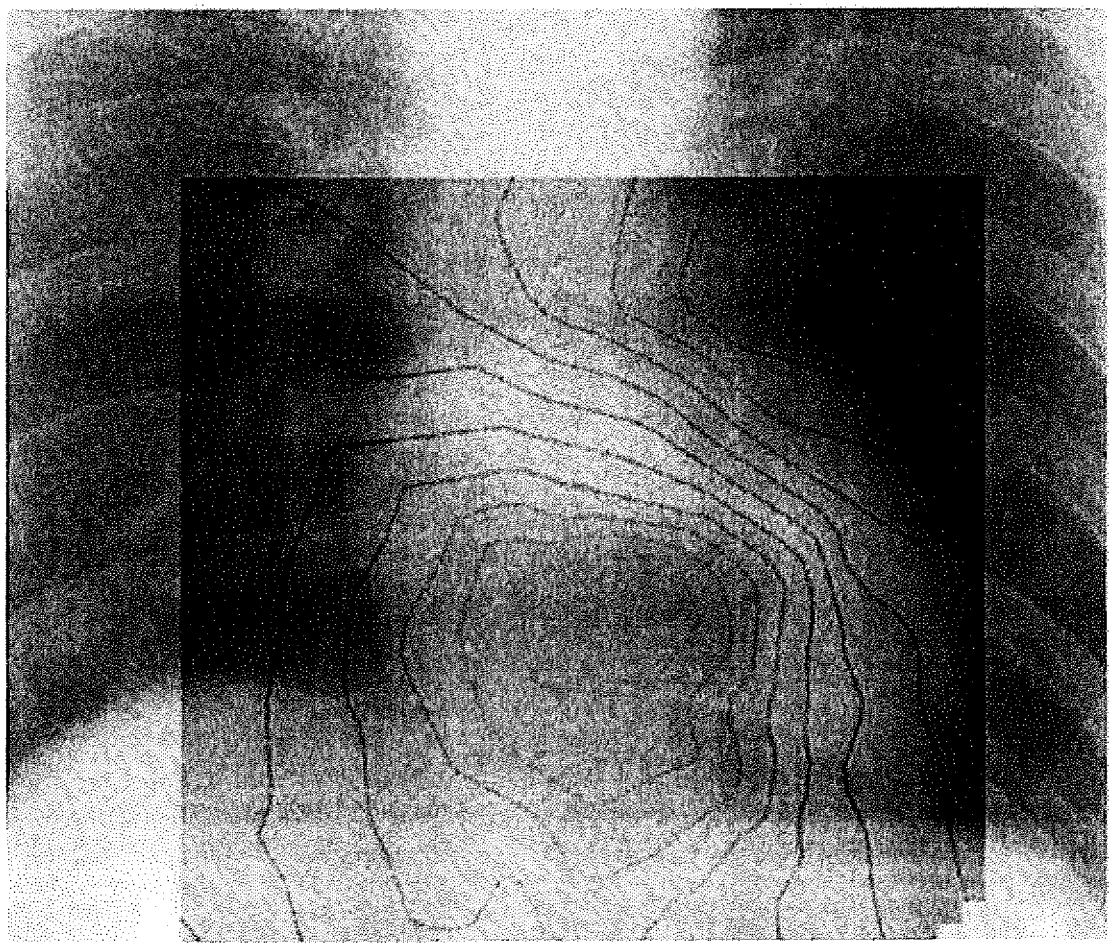
FIG. 4 is a diagram for illustrating measurement results in which biomagnetic measurement results and an X-ray image are superimposed.

Results of measuring the chest of a human using the biometric information measuring device 1 are shown in FIG. 4. As evident from FIG. 4, it is possible to obtain biometric information in which an X-ray image and a magnetocardiogram are superimposed in one measurement.

Remarkable effects of obtaining both an X-ray image of the chest of the subject S and a magnetocardiogram can be seen when performing group examinations. In traditional examinations with an electrocardiogram, a plurality of electrodes must be directly attached to the skin of the subject, which may place emotional burden on female patients and requires a person to be present to conduct the measurement. Examinations using an magnetocardiogram can be performed while wearing a T-shirt, which can greatly reduce stress placed on female patients. In addition, the work of the person performing the examination can be reduced because radiation images can be acquired in the same place as an examination by magnetocardiogram.

Herein, the site to be measured is not limited to the chest and may be another site or organ such as the brain or the spine.

EXPLANATION OF REFERENCE NUMERALS 1, 10 biometric information measuring device
2 biomagnetism detection unit
2a magnetic sensor
2b holding portion
3 radiation detection unit
4 radiation emission unit
5 support stand
6 control unit
7 support portion
7a support surface
8 angle adjustment mechanism
8a pedestal
8b rotational axis support frame
S subject

The invention claimed is:

1. A biometric information measuring device comprising:
a biomagnetism detection unit that can detect biomagnetism of a subject; and
a radiation detection unit that can acquire an image corresponding to emitted radiation as digital image data generated by means of a supply of a power source,
the biomagnetism detection unit including a plurality of magnetic sensors that can detect biomagnetism emitted from the subject, and a holding portion that holds the magnetic sensors,
the radiation detection unit being disposed between a measuring region of the subject and the biomagnetism detection unit, and
where the radiation detection unit is held by the biomagnetism detection unit.

2. The biometric information measuring device according to claim 1, further comprising a control unit that can perform control such that the radiation detection unit is not supplied with power while the biomagnetism detection unit is detecting biomagnetism.

3. The biometric information measuring device according to claim 1, further comprising a support stand that slidably supports the biomagnetism detection unit.

4. The biometric information measuring device according to claim 1, further comprising a support portion that supports the biomagnetism detection unit, the support portion including a support surface that can support the subject at an inclined posture.

5. The biometric information measuring device according to claim 4, wherein the support portion includes an angle adjustment mechanism that can adjust an angle of the support surface from a horizontal direction.

6. The biometric information measuring device according to claim 1, further comprising a radiation emission unit that irradiates the subject with radiation.

7. The biometric information measuring device according to claim 1, wherein the plurality of magnetic sensors can detect biomagnetism of the subject under a normal temperature environment.

8. The biometric information measuring device according to claim 1, wherein the plurality of magnetic sensors are removable magnetic sensors.

9. The biometric information measuring device according to claim 2, further comprising a support stand that slidably supports the biomagnetism detection unit.

10. The biometric information measuring device according to claim 2, further comprising a support portion that supports the biomagnetism detection unit, the support portion including a support surface that can support the subject at an inclined posture.

11. The biometric information measuring device according to claim 3, further comprising a support portion that supports the biomagnetism detection unit, the support portion including a support surface that can support the subject at an inclined posture.

12. The biometric information measuring device according to claim 2, further comprising a radiation emission unit that irradiates the subject with radiation.

13. The biometric information measuring device according to claim 2, wherein the plurality of magnetic sensors can detect biomagnetism of the subject under a normal temperature environment.

14. The biometric information measuring device according to claim 2, wherein the plurality of magnetic sensors are removable magnetic sensors.

* * * * *